(12) United States Patent
Spiertz (10) Patent No.: US 11,805,993 B2
(45) Date of Patent: Nov. 7, 2023

(54) VAGINAL SPECULUM

(71) Applicant: ComfortPat B.V., Huissen (NL)

(72) Inventor: Sasja Anne Huib Spiertz, Sittard (NL)

(73) Assignee: COMFORTPAT B.V., Huissen (NL)

( * ) Notice: Subject to any disclaimer, the term of this patent is extended or adjusted under 35 U.S.C. 154(b) by 1129 days.

(21) Appl. No.: 16/347,834

(22) PCT Filed: Nov. 7, 2017

(86) PCT No.: PCT/EP2017/078434
§ 371 (c)(1),
(2) Date: May 7, 2019

(87) PCT Pub. No.: WO2018/083330
PCT Pub. Date: May 11, 2018

(65) Prior Publication Data
US 2019/0254512 A1 Aug. 22, 2019

(30) Foreign Application Priority Data

Nov. 7, 2016 (NL) ..................... 2017733

(51) Int. Cl.
*A61B 1/303* (2006.01)
*A61B 1/00* (2006.01)
(Continued)

(52) U.S. Cl.
CPC .......... *A61B 1/303* (2013.01); *A61B 1/00096* (2013.01); *A61B 1/00101* (2013.01);
(Continued)

(58) Field of Classification Search
CPC . A61B 1/303; A61B 1/00096; A61B 1/00103; A61B 1/00105; A61B 1/04; A61B 1/06; A61B 1/32; A61B 1/31
See application file for complete search history.

(56) References Cited

U.S. PATENT DOCUMENTS 3,789,835 A 2/1974 Whitman
4,300,541 A * 11/1981 Burgin ................. A61B 1/0669
600/222
(Continued)

FOREIGN PATENT DOCUMENTS

CA 2260099 C 4/2007
CN 2633328 Y 8/2004
(Continued)

OTHER PUBLICATIONS

Priority Search report dated Mar. 9, 2017 for Dutch patent application NL2017733.
(Continued)

*Primary Examiner* — Tracy L Kamikawa
(74) *Attorney, Agent, or Firm* — Hoyng Rokh Monegier B.V.; David P. Owen (57) ABSTRACT

An assembly of a vaginal speculum and a reusable electric device. The vaginal speculum can be introduced into the vagina. A speculum housing has at least one spoon blade with an opened and closed state near a distal end. The spoon blade is operated by an operating device that is guided by and slides in the housing. The reusable electric device comprises a housing with an aperture and including a camera module near a distal end of the housing and a wireless communication module near a proximal end of the housing. The vaginal speculum and the reusable electric device share a connection system for releasably connecting the reusable electric device to the vaginal speculum. The connection system is formed on the operating device.

17 Claims, 6 Drawing Sheets (51) Int. Cl.
*A61B 1/32* (2006.01)
*A61B 1/04* (2006.01)
*A61B 1/06* (2006.01)

(52) U.S. Cl.
CPC ...... *A61B 1/00103* (2013.01); *A61B 1/00105* (2013.01); *A61B 1/32* (2013.01); *A61B 1/0014* (2013.01); *A61B 1/00163* (2013.01); *A61B 1/04* (2013.01); *A61B 1/06* (2013.01)

(56) References Cited

U.S. PATENT DOCUMENTS

| | | | |
|---|---|---|---|
| 4,905,670 A | | 3/1990 | Adair |
| 5,063,908 A | * | 11/1991 | Collins .................... A61B 1/32 |
| | | | 600/187 |
| 5,143,054 A | * | 9/1992 | Adair .................. A61B 5/4255 |
| | | | 600/122 |
| 5,503,617 A | | 4/1996 | Jako |
| 5,846,249 A | * | 12/1998 | Thompson ........... A61B 1/0669 |
| | | | 606/119 |
| 6,379,296 B1 | * | 4/2002 | Baggett ................. A61B 1/303 |
| | | | 600/179 |
| 7,371,212 B2 | * | 5/2008 | Klaassen ................. A61B 1/32 |
| | | | 600/222 |
| 8,267,860 B2 | * | 9/2012 | Klaassen .................. A61B 1/32 |
| | | | 600/222 |
| 10,045,683 B2 | | 8/2018 | Farr et al. |
| 10,376,138 B2 | | 8/2019 | McMahon et al. |
| 2006/0122463 A1 | | 6/2006 | Klaassen et al. |
| 2006/0281786 A1 | | 12/2006 | Hamprecht et al. |
| 2007/0179342 A1 | * | 8/2007 | Miller ..................... A61B 1/05 |
| | | | 600/199 |
| 2007/0230164 A1 | | 10/2007 | Vivenzio et al. |
| 2009/0198108 A1 | | 8/2009 | Chen et al. |
| 2010/0076344 A1 | | 3/2010 | Kecman et al. |
| 2010/0305406 A1 | | 12/2010 | Braun et al. |
| 2014/0142433 A1 | | 5/2014 | Greenstein et al. |
| 2016/0003800 A1 | | 1/2016 | McIntire et al. |
| 2016/0038012 A1 | | 2/2016 | McMahon et al. |
| 2016/0038014 A1 | | 2/2016 | Molnar |
| 2016/0262604 A1 | | 9/2016 | Greenstein et al. |
| 2016/0296109 A1 | * | 10/2016 | Nadershahi ............ A61B 1/015 |
| 2018/0014721 A1 | * | 1/2018 | Rullo ..................... A61B 1/303 |

FOREIGN PATENT DOCUMENTS

| | | |
|---|---|---|
| CN | 2011 64459 Y | 12/2008 |
| CN | 100488441 C | 5/2009 |
| CN | 102934984 A | 2/2013 |
| CN | 103298391 A | 9/2013 |
| CN | 203763046 U | 8/2014 |
| CN | 204428006 U | 7/2015 |
| CN | 105411518 A | 3/2016 |
| CN | 105658150 A | 6/2016 |
| CN | 205514520 U | 8/2016 |
| EP | 1343412 A1 | 9/2003 |
| JP | 2006-504466 A | 8/2006 |
| JP | 2016-154848 A | 2/2018 |
| WO | 9602195 A1 | 2/1996 |
| WO | 3147406 A1 | 7/2001 |
| WO | 2004039252 A | 5/2004 |
| WO | WO 2009 154779 A1 | 12/2009 |
| WO | WO 2012 010857 A1 | 1/2012 |
| WO | 2015/040570 A1 | 3/2015 |

OTHER PUBLICATIONS

International Search report dated May 13, 2018 for International application PCT/EP2017/078434.
International Preliminary Report on Patentability dated May 7, 2019 for International application PCT/EP2017/078434.

* cited by examiner fig 1 fig 2 fig 3 fig 4a fig 4b fig 5 fig 6 fig 7a fig 7b fig 8a fig 8b fig 8c fig 9

VAGINAL SPECULUM

FIELD OF THE INVENTION

The present invention relates to vaginal speculum for introduction into a vagina.

BACKGROUND

Vaginal specula generally include a pair of adjustable, longitudinally arranged spoon blades and handles. These blades are inserted into the vagina and pivotally adjusted to expand the vaginal cavity created/opened by the speculum. Specula are typically used by medical practitioners, especially obstetricians, gynecologists, and surgeons, to visually observe the vaginal walls, cervix or uterus, and to create a cavity within the body in which to perform various procedures.

Disposable vaginal speculum are available to allow low-cost access to many women in the world. Vaginal specula can be used by trained and untrained operators. The vaginal speculum can be used by a third person on a subject or the subject can insert the speculum herself.

A vaginal speculum with a body and a single spoon blade is known. EP 1343412 A1 describes a vaginal speculum and was taken as a starting point for further developments disclosed herein. EP 1343412 is included by reference in its entirety.

Several functions can be performed in combination with a speculum, which functions require more costly equipment, such as a camera function etc.

It is a goal to provide a speculum that allows one or more of the existing functions/properties/uses and to improve one or more properties of specula, in particular disposable specula. It is a further object to allow low-cost access to specula. It is a further object to provide a speculum with several functionalities that can be handled without difficulties. It is a further goal to provide a safe speculum. It is also a goal to provide hygiene in combination with a speculum. It is a goal to provide a speculum with one or more additional or improved functions. At least one or more of the above goals and objects are to be achieved with the current invention.

DESCRIPTION OF THE INVENTION

According to an aspect of the invention an assembly of a vaginal speculum and reusable electric device is provided. The reusable electric device is a device that provides one or more electrical functionalities, preferably electronic funcionalities, such as a camera function, a lighting function etc. The reusable electric device comprises an electric device housing with an aperture, a circuitry, e.g. comprising a battery, received in the electric device housing. The housing surrounds the one or more functionalities. Light can enter or can be emitted through the aperture in the housing. The aperture can be a transparent housing part or a window. In an embodiment the electric device has a lens having a focal distance, and wherein the dimensions of vaginal speculum and the electric device are such that, in use when the spoon blade is opened, the lens is positioned internal of the vagina.

The electric device is reusable in that it can be used during different insertions into the vagina. The vaginal speculum can be a disposable speculum.

According to embodiments of the invention the vaginal speculum is arranged to be introduced into a vagina. The vaginal speculum comprises a speculum housing and at least one spoon blade for providing an opened and closed state of the vaginal speculum. In the closed state the vaginal speculum is inserted into the vagina and can be removed from the vagina. When inserted, the blade can be moved to an opened state allowing viewing through the housing into the vagina.

In embodiments the vaginal speculum will have a proximal end and distal end, the speculum housing having a longitudinal direction, the housing arranged to allow viewing in the longitudinal direction towards the distal end. Thereto the housing has a viewing opening that allows the user to view. The housing is hollow to allow viewing of the distal end. The viewing window, that is the opening at the distal end through which internal parts of the woman are inspected, is enlarged by opening the spoon blade, allowing to view internal parts of a woman.

In embodiments the speculum housing will have a housing part that extends in the longitudinal direction. The speculum housing will have an exterior surface that can be in contact with the vaginal walls. The one or more interior surfaces of the housing of the speculum surround the viewing opening. Preferably that housing part has a O, C or U shaped cross-section perpendicular to the longitudinal direction.

The electric device is preferably an independent electric device having an electrical source such as a battery and/or a wireless receiver for receiving energy for operating one or more of the electrical functions. This allows obtaining the vaginal speculum that operates without connections to the outside, which could be hampering the positioning of the speculum and that could exert a force on the vaginal speculum once inserted.

According to embodiments of the invention, the vaginal speculum and the reusable electric device have a connection system. The connection system allows mounting the reusable electric device to the speculum. The reusable electric device is mounted to the speculum such that on the one hand the reusable electric device is operated in an optimum way and on the other hand a significant part of the field of view through the speculum remains available to the user. The independent electric device, without connections to the outside reduces the force needed for positioning.

In some embodiments the electric device comprises a connecting wire that can be externally connected to a interface or control device, such as a computer. This wired connection would be in place of a preferred wireless connection. The wireless or wired connection allows controlling one or more electric functions of the electric device.

In embodiments, the connection system comprises a guiding rail. The connection system allows to releasably connect the reusable device. The connection system allows releasable locking of the reusable device to the vaginal speculum. The connection system allows connecting the electric device to the speculum and mounting it into position during insertion and use of the vaginal speculum.

The connection system will have an insert direction for inserting the reusable electric device. The insertion direction of the connection system extends generally from the proximal end to the distal end. The insertion direction can be parallel is to the viewing direction. This provides the user with an intuitive design.

Further in embodiments of the invention, the connection system is preferably arranged to position the reusable electric device in the vaginal speculum housing along said speculum housing part. Accordingly the electric device is inserted into the housing towards the distal end positioning it closer to the area that is to be inspected. By mounting the reusable device along an interior housing part of the speculum housing that extends in the longitudinal direction, the field of view hardly diminishes. This also allows positioning the electric device closer to the distal end of the speculum, which is closer to the viewing window. In turn this allows closer inspection.

Preferably the connection system is positioned proximal from the spoon blade, in particular proximal from a hinge connecting spoon blade to the housing. Preferably the connection system is arranged such that, in use, the distal end of the reusable electric device is positioned proximal from the spoon blade, e.g. a hinge connection of the spoon blade to the housing. As a result, even after opening the spoon blade, in use the electric device is surrounded by the housing, e.g. preventing contact with female tissue.

Preferably, in use, the electric device is positioned such that a distal end and a proximal end of the electric device are less distal and less proximal than respective ends of the housing. Accordingly the electric device is surrounded by the housing.

In embodiments, in use, the proximal end of the reusable electric device are positioned external of the vagina. Preferably the connection system is arranged to keep the proximal end of the electric device external from the vagina. In embodiments the speculum will have a device on its housing, such as a notch, a stop or spreading wings, that are arranged to not enter the vagina and the proximal end of the electric device installed in the connection system is held more proximal than that device.

In preferred embodiments the housing part, along which the reusable device is positioned, is brought internally of the vagina during use. This positions the electric device in use internally, or at least mostly. It is possible that in use a proximal end of the electric device is external of the vagina. The housing part, along which the electric device is positioned, is positioned closer to the distal end than the most distal part of the vaginal speculum arranged to remain outside of the vagina. Preferably said housing part is arranged proximal from the spoon blade. Preferably a hinge that connects the spoon blade to the housing is arranged more distal than said housing part.

Preferably the housing, an in particular said housing part along which the electric device extends, will have a constriction on an outside surface thereof arranged to engage a ring of muscle tissue formed by the musculus sphincter ani externus and/or the musculus puborectalis when inserted. In general the constriction can engage the pelvic floor. Preferably the vaginal speculum has a housing part that has on an outside surface thereof the constriction and along an interior surface the reusable device positioned.

Preferably the constriction is arranged proximal from the spoon blade and even more preferably closer to the distal end than the most distal part of the vaginal speculum arranged to remain outside of the vagina. Preferably a hinge that connects the spoon blade to the housing is arranged more distal than the constriction. Accordingly the muscle engage the constriction on the housing part, positioning the hinge and spoon blade more internal, resulting in a lower force to open the spoon blade.

In embodiments the cross-section transverse to the longitudinal direction at said speculum housing part is generally O-shaped. The housing part will have high rigidity. The connection system positions the reusable electric device within and close to the O-shaped housing part. During use said housing part has a constant circumference.

In embodiments the housing is further arranged to allow introduction of a smearing device. The smearing device allows taking samples. The smearing device can be introduced in combination with the reusable electric device being mounted in the vaginal speculum. In a preferred embodiment the housing is arranged to support the smearing device such that a distal end thereof and a focal point of the electric device generally coincide. This will allow viewing of the sample area via the electric device and at the same time taking the sample.

In embodiments, the spoon blade is connected to the speculum housing via a hinge, wherein the vaginal speculum has part arranged to remain outside of the vagina in use (when inserted into the vagina), wherein the hinge is arranged closer to the distal end than the most distal part arranged to remain outside of the vagina.

In examples the speculum housing with the spoon blade in closed state will generally have a converging shape towards the distal end thereof. This increases the user-friendliness.

In order to operate a vaginal speculum, e.g. a dilation, but preferably to operate the spoon from the closed to the opened state, the vaginal speculum has an operating device. The operating device can be embodied as a pushing rod. The operating device is held in a guide and can slide in the housing. In embodiments of the invention the connection system is at least partially formed on the operating device. In such embodiments the reusable electric device is mounted to the operating device and can be moved together with it. This allows mounting the electric device to the operating device of the vaginal speculum in a first position with respect to the housing. Subsequently the speculum is inserted into the vagina and the operating device is operated by moving it toward the distal end of the vaginal speculum, e.g. pushed further into the vagina. As a result the electric device is also moved toward the distal end of the speculum and is brought closer to the area to be surveyed.

Preferably the operating device and reusable device are positioned at a top side of speculum housing to reduce contamination. As a result of gravity vaginal fluids will mostly collect on the lower side of the speculum housing, at a distance from the mounting position of the reusable device.

In embodiments the operating device is a rod for operating the spoon. The operating device and the spoon blade can have a locking system for connecting them. This is a preferred constellation for lowering the assembly costs. The locking system can comprise simple interlocking notches received in a receiving space formed during molding the operating device and spoon blade. No glue or other adhesive is used to connect the operating device and spoon.

In embodiments the operating device comprises a proximal arm and a distal atm connected via a hinge, the proximal atm being connectable to the spoon blade. This further hinging the spoon blade around a first hinging point and hinging the two part operating device via its own hinge between the two arm parts.

In embodiment the operating device comprises a ratchet mechanism arranged to maintain a position of the operating device after operation by the user and a decoupling device that can be operated by the user for decoupling the ratchet mechanism allowing the ratchet mechanism to reset.

In embodiments where the connection system is on the operating device, it is further useful that the operating device has near a proximal end thereof an operating device notch arranged to be engaged by the operator to operate the operating device and wherein the connection system is arranged to position a proximal end of the reusable electric device near the operating device notch. The operator, e.g. in case of self-inspection, will engage the notch of the operating device with the fingers of one hand. Those same fingers, or one of those fingers, will be able to, without having to move the hand, operate both the operating device and the reusable electric device. With one hand both the operating device e.g. for operating the spoon and the reusable electric device, can be operated. The reusable electric device can have interface means near the proximal end positioned close to the operating device notch. The operating device notch and the proximal end of the reusable electric device are arranged more proximal than any of the parts of the vaginal speculum arranged to remain outside of the vagina in use.

Accordingly a speculum can be provided that is a fertility monitor. More generally a speculum is provided that has health monitoring qualities. It is e.g. possible to add detection mechanisms for detecting or monitoring health risks such as cancers or infections. The intelligent speculum and assembly according to the invention can function as a basis for tele-gynecology.

According to an aspect of the invention an reusable electric device is provided. The reusable electric device can be fitted in a vaginal speculum. The electric device has a housing in which one or more electrical devices are received. One electrical device is a sensor that is directed in a distal direction. The housing further has a connection system for allowing the electric device to be connected along a housing part of the vaginal speculum by being inserted in the distal direction, wherein a proximal end of the housing comprises one or more interface devices for controlling the one or more electrical devices. This allows positioning the reusable electric device onto a vaginal speculum with the sensor directed at the area to be surveyed, the housing of the electric device connected to the vaginal speculum and with the interface device still being at the disposal of the operator, preferably outside the vagina.

The electric device can have, as a safety measure, a temperature sensor and a control circuitry, wherein the control circuitry is arranged to take action if the temperature sensor measures a temperature above a predetermined safety temperature.

Any of the features described, any of the advantages described herein can be combined in a single embodiment, unless explicitly indicated that such can not be done. The dispensing system or closure system of this invention is suitable for use with a variety of conventional or special containers having various designs, the details of which, although not illustrated or described, would be apparent to those having skill in the art and an understanding of such containers. It will also be understood by those of ordinary skill that novel and non-obvious inventive aspects are embodied in the described exemplary dispensing system, but also in the not-explicitly described possible combinations of features disclosed herein.

The invention will be described in more detail with reference to preferred embodiments shown in the figures. However the invention is in no way limited to the disclosed or shown embodiments. Identical or similar features are indicated with the same reference numeral.

DESCRIPTION OF THE FIGURES

Figure 1:
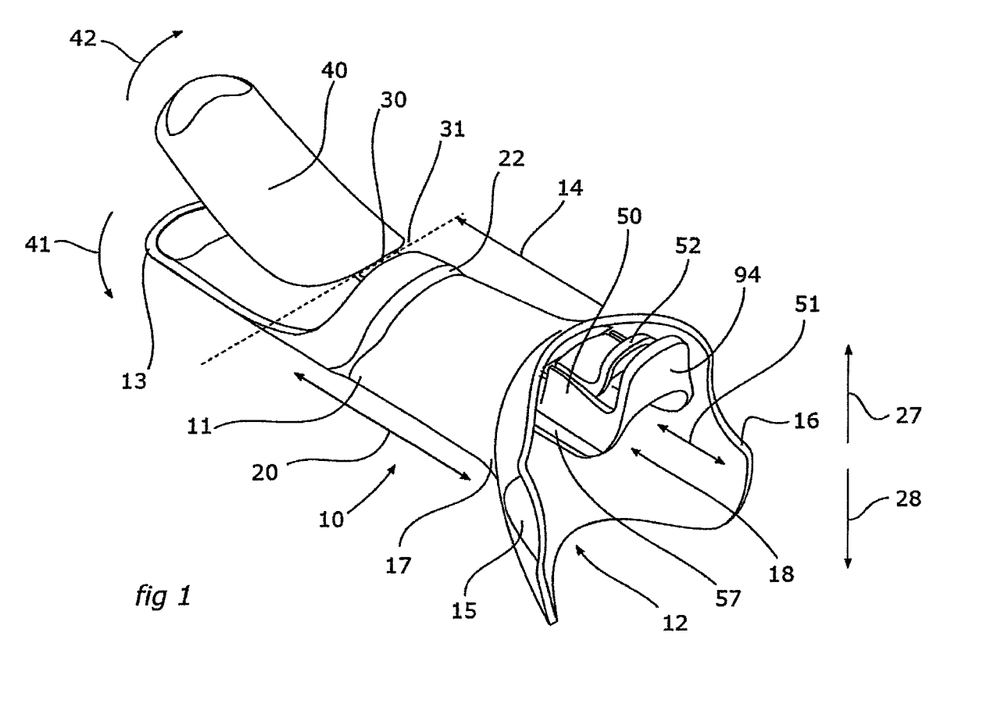
FIG. 1 shows a three dimensional view of an embodiment of a vaginal speculum according to the invention.

FIG. 1 shows a speculum 10. The main housing 11 is shown. Main housing 11 has a proximal end 12 and a distal end 13. The main housing 11 can be manufactured as a single piece in injection molding. However many different options are available. A main housing 11 comprising several separately manufactured, but connected, parts can also be part of the invention.

Distal end 13 is to be inserted into the vagina. Proximal end 12 remains outside of the vagina. Arrow 14 indicates the general insertion direction.

Near proximal end 12 the main housing 11 widens and comprises in the illustrated embodiments two ears 15,16 arranged to engage and spread the labia or push aside pubic hair of the patient. The ears 15,16 are also arranged as stops to prevent further insertion into the vagina. Especially proximal from point 17, the vagina speculum housing 11 is arranged to not enter the vagina. Proximal from point 17 the housing significantly diverges outwards, acting as a stop. Further stops or notches can be present to prevent or stop deeper insertion into the vagina.

Hinge 30 connects the main housing 11 to the spoon blade 40.

Distal from point 17, a housing part 20 of the main housing is formed similar to a tube. Especially main housing part 20, which starts distal from point 17 and extends up to proximal of hinge 30, the housing is O-shaped in cross-section. In other embodiments the housing is C-shaped or U-shaped. Circular, oval and other hollow cross-sections are possible. The cross-sectional direction is perpendicular to the insertion direction 14. The hollow housing 11 allows viewing through the interior open area indicated by arrow 18 in the insertion direction 14 towards the distal end 13.

On housing part 20 a constriction 22 can be present. Constriction 22 will be positioned internally of the vagina in use and is arranged to engage the musculus sphincter ani externus and/or the musculus bulbocavernosus. This will allow inserting the speculum in the vagina and maintaining the speculum position without providing a internally directed force. The internal vaginal muscles will engage the constriction to hold the speculum in its inserted position. Since spoon blade 40 is more distal than the constriction, opening the spoon blade when inserted beyond the indicated muscles requires less force.

Further ribs (not shown) can be present. Ribs are preferably formed on the under side of the speculum. Upper side is indicated by arrow 27. The bottom side is indicated by arrow 28.

A hinge 30 or any other connection can be present to connect a spoon blade 40 to the housing 11. In embodiments of the invention two spoon blades can be present. The hinge 30 can formed as a lip formed from the same plastic material as the housing and/or the spoon, the lip being formed thinner, such that it can be bended.

The hinge 30 allows opening of the spoon blade(s). Hinge 30 allows hinging around hinge axis 31. In the shown embodiment the spoon blade is not closed. The spoon blade 40 can be brought to a closed position by moving is according to arrow 41 with respect to housing 11. The spoon blade 40 can also be brought to a more open state, by moving it according to arrow 42.

To operate the spoon blade 40 while inserted in the vagina, an operating device 50 is present. The operating device 50 can also be arranged to operate another function of the speculum, e.g. dilation.

Operating device 50 is mounted in housing 11 and can slide according to arrow 51 with respect to housing 11. On the inner side of housing 11, preferably in the C or O-shaped part of the housing that has not dilation function, a guide for sliding the operating device is formed. A user can operate the operating device 50 by engaging a proximal end 49 thereof, formed by notch 94.

Operating device 50 is connected to the spoon blade 40. By moving the operating device 50 towards the distal end 13, along direction 51, the spoon blade 40 is moved in direction 41. Moving the operating device 50 in the opposite direction can move spoon blade 40 in direction 42. To provide the force needed for operation, the user can engage both notch 94 and housing 11 to push in either direction 51.

In embodiments a ratchet mechanism can be present to lock the operating device and thereby spoon blade 40 in a opened positioned. Although the details of the ratchet mechanism are not shown in FIG. 1, an unlocking device 52 is shown. This unlocking device 52 allows disengaging the ratchet such that moving the operating device is possible again and e.g. the spoon blade can be move from an opened position back to a closed position. In the shown embodiment unlocking device 52 can be pushed in direction 28 to unlock the ratchet. Pushing the unlocking device 52 in direction 28 with respect to the operating device 40, will result in a hinging movement due to flexibility. As will be discussed in relation to FIG. 5, teeth 59 of the unlocking device will disengage allowing backwards movement of the operating device with respect to the housing.

On operating device 50 a rails 57 is formed that is part of a connection system to mount a reusable electric device 70 to the speculum. In the shown embodiment the connection system is on the operating device 50, but in other embodiments the connection system/rails 57 can be formed on the housing 11.

Figure 2:
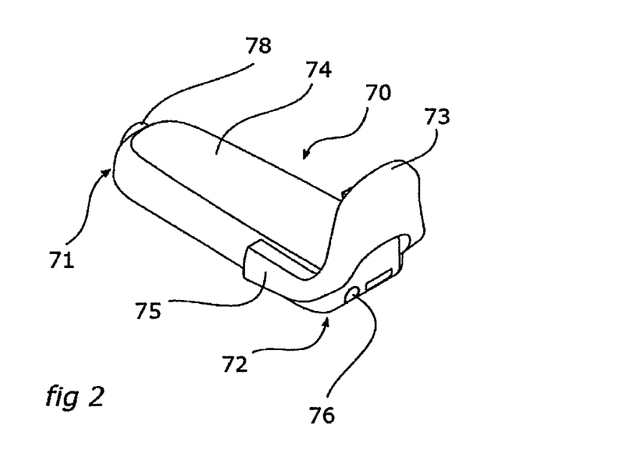
FIG. 2 shows a reusable electric device according to the invention.

A reusable electric device 70 is shown in FIG. 2. The reusable electric device 70 has a housing 74 with a distal end (arrow 71) and proximal end (arrow 72). Notch 73 is formed on housing 74 at the proximal end. Interface device 76 are formed at the proximal end 72. Near the distal end 71 an aperture or window 78 can be formed for light to enter or exit the reusable electric device 70. Inside the housing a battery, a sensor, a light etc. can be present. Light can be emitted through window 78 or the sensor, such as a CCD or CMOS can detect light entering through window 78. The electrical devices in the reusable electric device can be operated by one or more interface units 76.

Figure 8A:
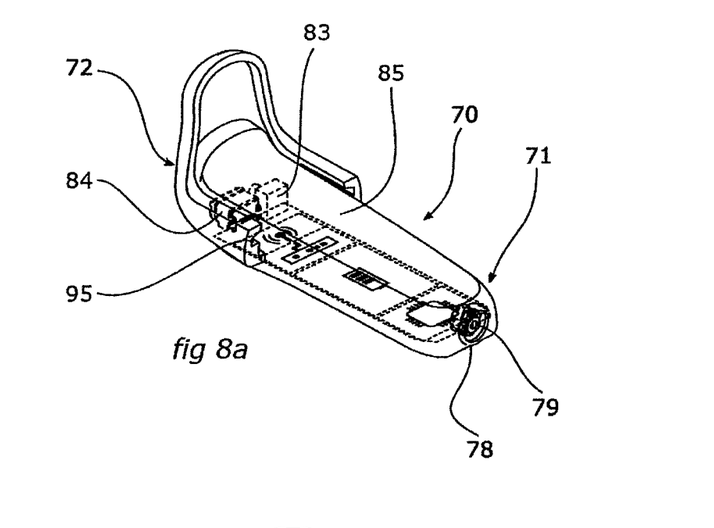
FIGS. 8a-8c show a reusable device according to an embodiment of the invention.

Wings 75 on opposite sides of housing 74 of the reusable electric device 70 are arranged to engage the rails 57 on the operating device 50. Wings 75 and rails 57 form the connection system for mounting the electric device 70 to the vaginal speculum. FIG. 8a shows in more detail the receiving space 95 in which rails 57 is received. All are part of and examples of a connection system for an electric reusable device to a speculum.

Operating device 70 is shaped such that the housing 74 is received under and between it. The rails 57 and wings 75 are formed such that they can engage and that the electric device 70 can be moved in the insertion direction 51 in order to mount the electric device to the speculum 10.

In use the window 78 is positioned close to the distal end 13, wherein the interface unit 76 is positioned near the proximal end 12. Notch 73 will prevent that the housing 74 is inserted too far. Window 78 is positioned in use proximal from hinge 30.

Clearly many different embodiments are possible to form a suitable connection system for mounting the reusable device to the speculum. In embodiments the housing 11 or housing part 20 has parts of the connection system. The connection system can comprises a lock for holding the mounted electric device in a predefined position.

Figure 3:
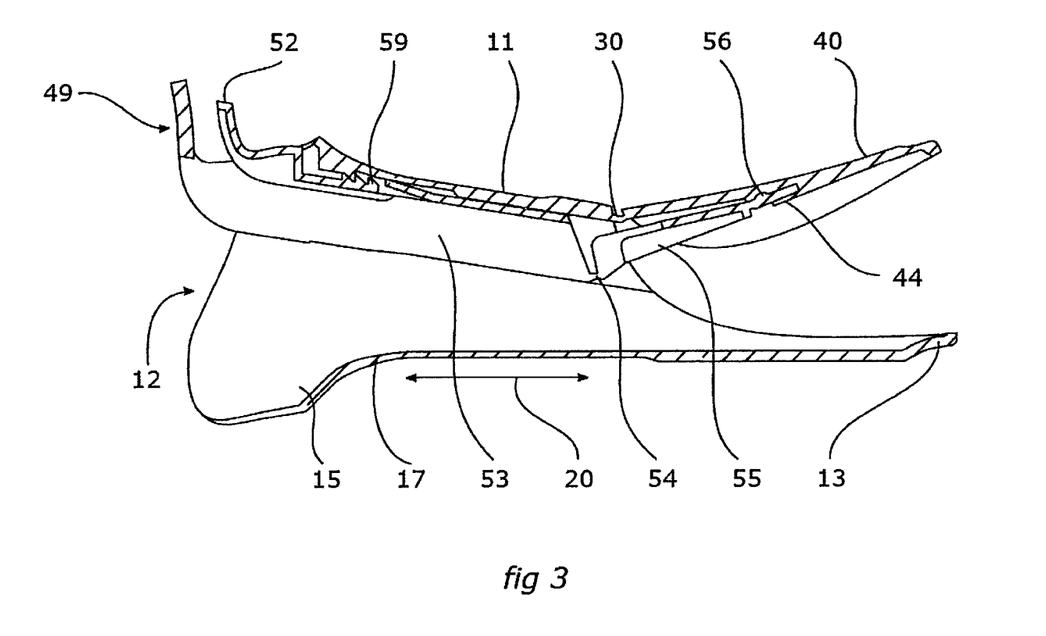
FIG. 3 shows a partially exploded side view of an assembly of a speculum according to the invention.

FIG. 3 shows the operating device 50, spoon blade 40 and housing 11 in more detail, with the spoon blade 40 in an opened state. The electric device 70 is not mounted. On the inside of housing part 20, operating device 50 is mounted slidable. Operating device 50 comprises a first arm 53 and a second arm 55 connected via a hinge 54. First arm 53 will move in generally longitudinal direction when operated.

Near the distal end of second arm 55, a locking unit 56 is formed that engages a locking unit 44 formed on the interior side of spoon blade 40. Locking units 44 and 56 are connected such that a movement of operating device 50 corresponds with hinging of spoon blade 40 according to arrows 41 or 42.

Ratchet tooth 59 is shown that is part of the ratchet mechanism to hold the operating device 50 in an inserted position. Ratchet tooth 59 can engage counter teeth 58 formed on the interior surface of housing 11. Unlocking device 52 is hingeable connected to operating device 50, here first aim 53. The unlocking device 52 has teeth 59.

Unlocking device 52 and notch 94 are positioned close together. This allows the user to operate either of them with a single hand using the fingers. Unlocking device 52 can be pushed downwards 28 to unlock the ratchet mechanism, resulting in the possibility to move the operating device backward/outward. This in turn will result in closing of the spoon blade. In embodiments the connection between operating device 50 and spoon blade 40 is disconnected when the operating device 50 is moved in the proximal direction.

Figure 4A:
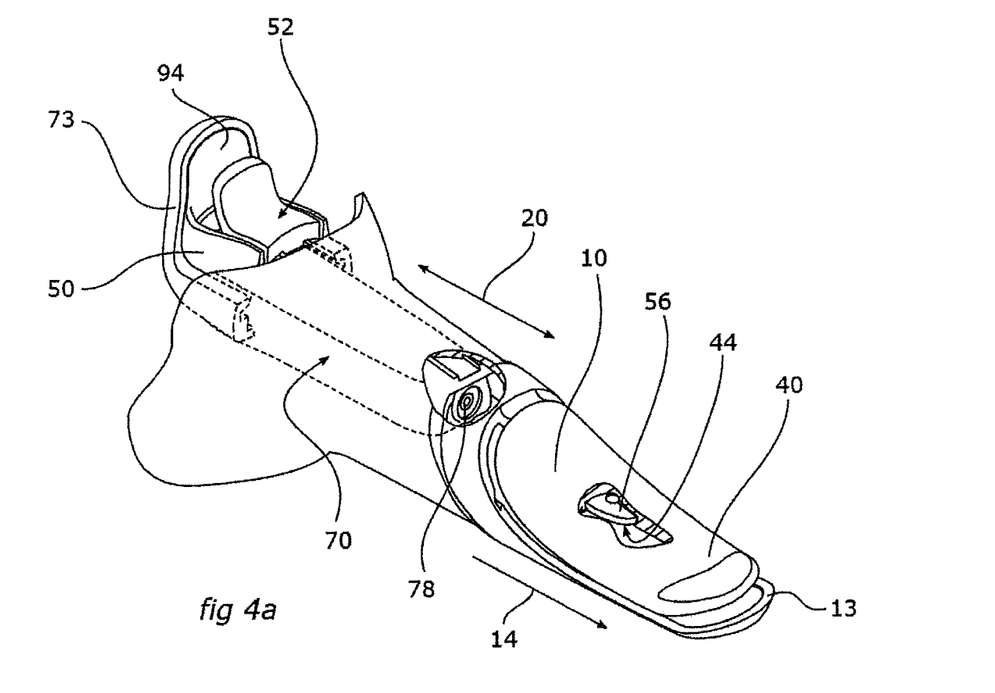
FIG. 4a shows a cross-sectional view of an assembly according to the invention.
Figure 4B:
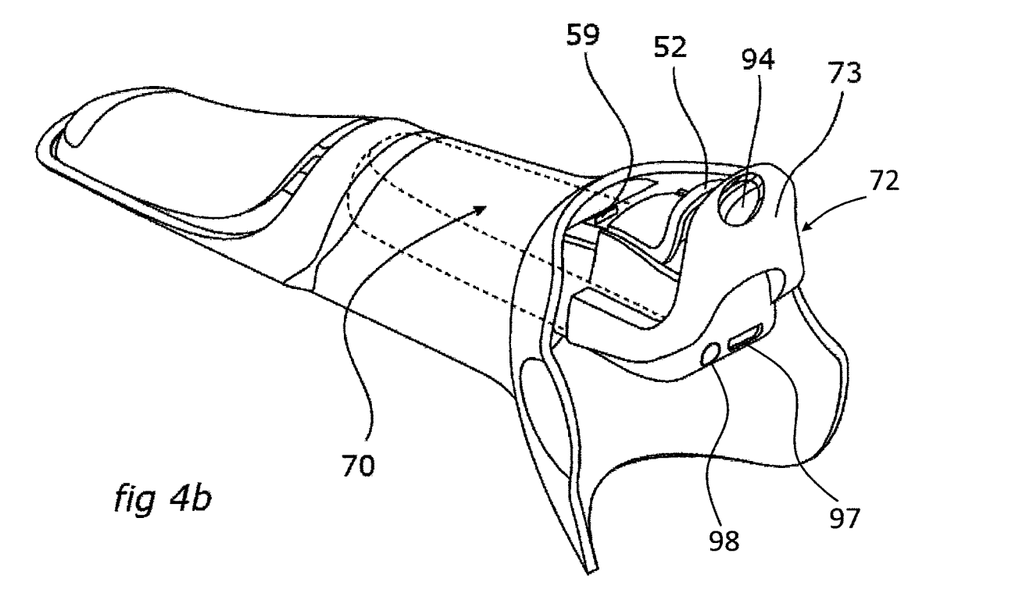
FIG. 4b shows partially exploded view of an assembly according to the invention.

FIGS. 4a and 4 shows a somewhat similar embodiment in which the same reference numerals are used to indicate similar parts. FIG. 4a shows the assembly of speculum 10 and reusable electric device 70 in mounted position. The spoon blade 40 is shown in closed state.

Housing part 20, which will be internally in the vagina in use, is O-shaped in cross section. Along an inside surface of the housing part 20 both the operating device 50 and the electric device 70 can be mounted, reducing the field of view of a user through the internal cavity of the housing 11 only in a very limited way. Housing part 20 can be O-shaped or C-shaped. In embodiments the cross section of housing part 20 is variable to be adjusted to the size of the vagina.

As one can see, distal end 71 of the electric device is positioned close to the distal end 13 of the speculum 10. This positions the electric device close to the area that is to be inspected. Operating the operating device by pushing it further inwards according to arrow 14, will bring the electric device even closer. However the distal end 71 of the electric device is preferably positioned proximal from hinge 30, also when the spoon blade is opened. This will result in a protective arrangement inside the housing part 20.

Although an example of a connection system between electric device 70 and operating device 50 is shown using a guide or rails, clearly different embodiments are possible.

Notch 94 is a proximal part of the operating device 50. Notch 94 and notch 73 are shaped to correspond. If the electric device is connected a single notch 94/73 is formed. The user can operate the operating device 50 using the single notch 94/73, securing that both the electric device and the operating device are moved in the insertion direction 14.

In the embodiment of FIG. 4b, the proximal end 72 of the electric device 70 is provided with a terminal 97 for making a wired connection. This terminal 97 can be a USB connector. Clearly many different wired connection are possible. Further a LED indicator 98 is shown. This indicator can e.g. indicate the status of a battery and/or the operation or standby mode of the electric device. The LED can have different colors and can emit light continuously or intermitted. Additional to the embodiment with terminal 97, or replacing the terminal 97, could be a wire that enters the housing 74 near the proximal end 92. The wire can have a connecting end, e.g. a USB connector, for connection to an external device, such as an interface or control device, e.g. a computer. Functions of the electric device 70 can be controlled from the interface or control device, instructions being send through the wire. Measurements and/or data acquired by the electric device 70 can be sent via the wire to the interface or control device. In other embodiments a wireless connection to an interface or control device is employed.

Figure 5:
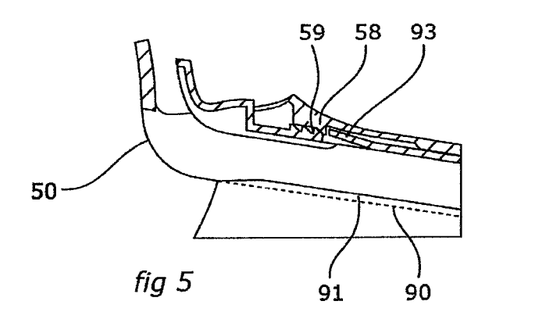
FIG. 5 shows a partially exploded view of a detail of an assembly according to the invention.

FIG. 5 shows operating device 50 having a rails 91 that is guided in a guide 09 formed in the interior surface of housing 11.

Further FIG. 5 shows tooth 58 formed on the interior side of housing 10 to form the ratchet mechanism.

Part of the first arm part 51 of operating device 50 is arm 93, which together with tooth 58 act as a stop in the proximal direction, preventing the user to remove the operating device 50 from the speculum.

Figure 6:
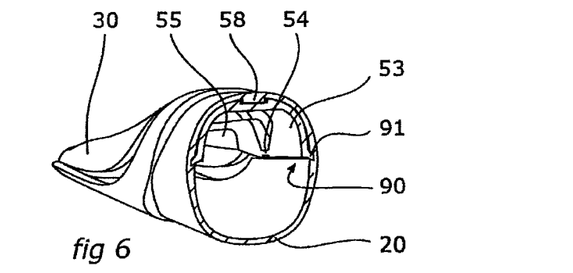
FIG. 6 shows a vaginal speculum according to an embodiment of the invention.

FIG. 6 shows an O-shaped cross section of housing 11 at housing part 20. Housing part 20 has a guide 90 for rails 91 of operating device 50.

Since housing part 20 is formed generally O-shaped and converges towards the distal end, an electric device 70 can be used that also generally converges towards the distal end. This will reduce the amount the electric device blocks the view of view.

Figure 7A:
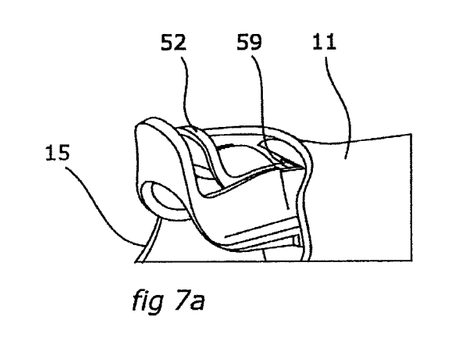
FIGS. 7a-7b show details of a vaginal speculum of the invention.
Figure 7B:
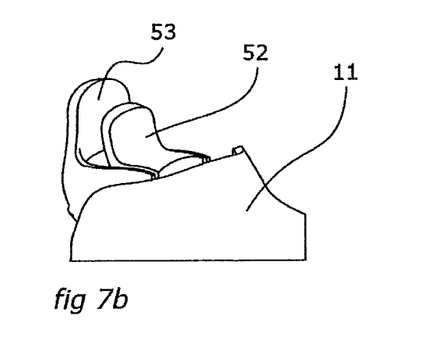

FIGS. 7a and 7b shows further details of the operating device 50.

Figure 8B:
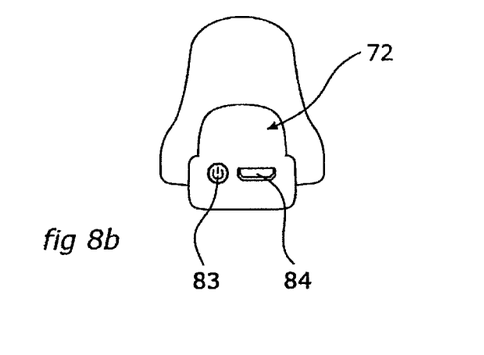
Figure 8C:
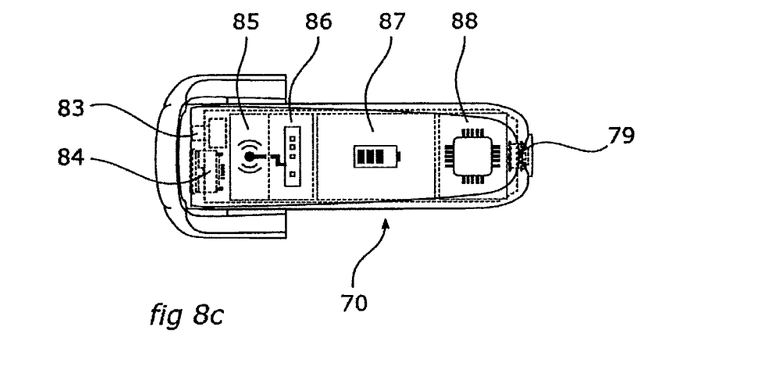

FIGS. 8a-8c show details of the reusable electric device 70. In window 78 a lens/camera module 79 or other device can be positioned. FIG. 8b shows a view of the proximal end 72, showing interface device, here formed by a on/off button 83 and a USB connection port 84. The button 83 allows starting and stopping a function of the electric device, e.g. start/stop video. The start/stop button can include a light (LED) to indicate the on/off state of the device. FIG. 8c shows a top view.

The reusable electric device 70 comprises an internal PCB, which is not shown in detail. The one or more PCB comprise different modules for providing different functionalities. In an embodiment the electric device 70 comprises inside the housing 74 beside a battery (87):

a camera module 79 coupled to a image processor module 88;

a communication module 86, that can include a WIFI module 85 and/or an USB module having a USB connection 84.

The two or more modules can be connected via a processor (not shown). More modules can be received in the housing, such as a transceiver and i/o interface, and on/off module, connected to the on/off switch 83. The communication module allows to output a signal from the camera module 79.

The communication module can include a transceiver. In embodiments the antenna, in the embodiment of FIG. 8c a WIFI antenna, is locate more proximal than the battery. The on/off switch 83 and I/O interfaces such as the USB port 84 are positioned more proximal than the battery and more proximal than the antenna 85. In embodiments of the invention the communication module 86 is located near the proximal end 72 of the reusable device. In an embodiment the battery 87 is positioned more distal then the communication module 86.

The electric device 70 can comprise several safety features. In embodiments a temperature sensor is received in the housing 74, preferably close to the battery 87. The sensor can be connected to the processor. If the sensor senses a temperature above a predetermined threshold, e.g. 70 degrees Celsius, the processor can stop the operations of the electric device as a safety precaution. The sensor allows sensing (over-)heating of the battery and functions as a safety measure. In embodiments the battery is received or embedded in further material inside the closed-off housing.

In other embodiments the communication module 86 and wireless module 85 are not present. A wired connection from the camera unit 79 is provided that exits the housing 74 at the proximal end 73, the wire being connectable to an interface or control device such as a computer.

Figure 9:
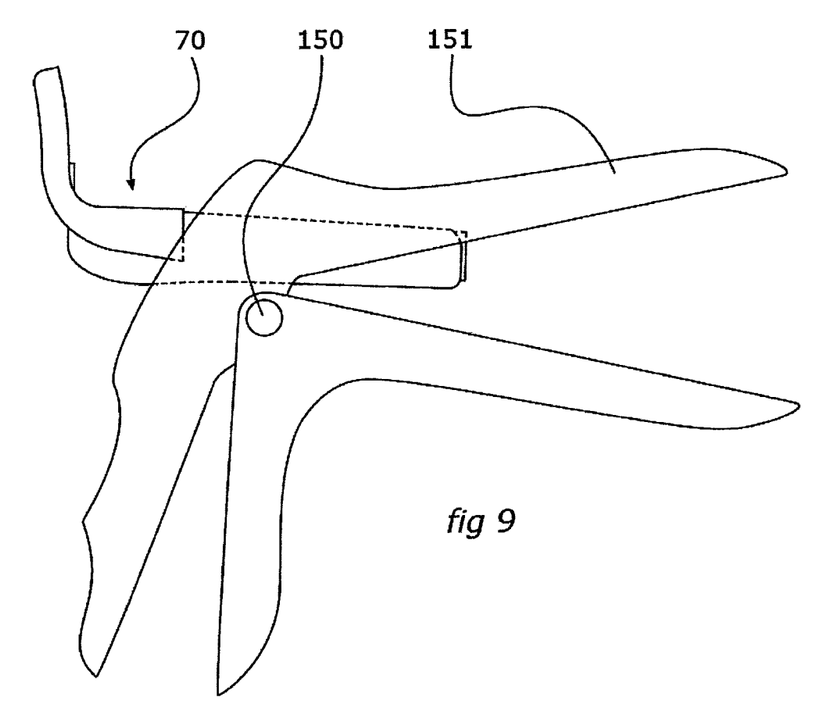
FIG. 9 shows a prior art speculum with a reusable electric device according to an embodiment of the invention.

FIG. 9 shows a prior art speculum having two spoon blades. A hinge 150 connects the blade. Inserting a similar electric device 70 in a prior art device in a similar manner as described above results in blocking the view through the speculum.

The invention claimed is:

1. An assembly of a vaginal speculum and a reusable electric device, wherein the vaginal speculum is arranged to be introduced into a vagina, the vaginal speculum comprising a speculum housing and at least one spoon blade for providing opened and closed states of the vaginal speculum, the vaginal speculum having a proximal end and a distal end, the speculum housing having a longitudinal direction, the housing arranged to allow viewing in the longitudinal direction towards the distal end, wherein a speculum housing part extends in the longitudinal direction, wherein the vaginal speculum has an operating device slidably mounted in the speculum housing for operating the at least one spoon blade from the closed state to the opened state by sliding within the housing generally along the longitudinal direction, wherein the reusable electric device has functional modules including at least a camera and a wireless communication module, and comprises an electric device housing with an aperture, and a circuitry received in the electric device housing, wherein a battery and the functional modules are received in the electric device housing, including at least the camera near a distal end of the electric device housing and the wireless communication module near a proximal end of the electric device housing, wherein the vaginal speculum and the reusable electric device have a connection system for releasably connecting the reusable electric device to the vaginal speculum, the connection system having an insert direction for inserting the reusable electric device, the insert direction extending from the proximal end of the vaginal speculum to the distal end of the vaginal speculum and the connection system arranged to position the reusable electric device in the vaginal speculum housing along said speculum housing part, wherein the connection system is at least partially formed on the operating device.

2. The assembly according to claim 1, wherein the at least one spoon blade is connected to the speculum housing via a hinge, and wherein the connection system is arranged to position a distal end of the reusable electric device proximal, or at most 1 cm distal, of that hinge.

3. The assembly according to claim 1, wherein the connection system is arranged to position a proximal end of the reusable electric device more proximal than parts of the vaginal speculum that are arranged to remain outside of the vagina in use.

4. The assembly according to claim 1, wherein the wireless communication module is free of external wired connections.

5. The assembly according to claim 1, wherein a cross-section transverse to the longitudinal direction at said speculum housing part is hollow, and the connection system positions the reusable electric device within the hollow speculum housing part.

6. The assembly according to claim 5, wherein the speculum housing part has a constriction on an outside surface thereof arranged to engage a ring of muscle tissue formed by the musculus sphincter ani externus and/or the musculus puborectalis when inserted into the vagina.

7. The assembly according to claim 1, wherein the reusable electric device has a lens having a focal distance, and wherein the dimensions of the vaginal speculum and the reusable electric device are such that, in use when the at least one spoon blade is opened, the lens is configured to be positioned internal of the vagina.

8. The assembly according to claim 7, wherein the speculum housing is further arranged to allow introduction of a smearing device, wherein the speculum housing is arranged to support the smearing device such that a distal end thereof and a focal point of the lens of the reusable electric device generally coincide.

9. The assembly according to claim 1, wherein the at least one spoon blade is connected to the speculum housing via a hinge, wherein the vaginal speculum has parts arranged to remain outside of the vagina in use when the vaginal speculum is inserted into the vagina, wherein the hinge is arranged closer to the distal end of the vaginal speculum than a most distal part of the parts of the vaginal speculum arranged to remain outside of the vagina in use.

10. The assembly according to claim 1, wherein the speculum housing and the at least one spoon blade in the closed state of the vaginal speculum generally have a converging shape towards the distal end of the vaginal speculum.

11. The assembly according to claim 1, wherein the vaginal speculum is a disposable vaginal speculum.

12. The assembly according to claim 1, wherein the operating device is embodied as a pushing rod.

13. The assembly according to claim 12, wherein
    the operating device and the reusable electric device are positioned at a top side of the speculum housing to reduce contamination, and/or
    the operating device and the at least one spoon blade have a locking system for locking the at least one spoon blade in a position, and/or
    the operating device comprises a proximal arm and a distal arm connected via a hinge, the distal arm being connectable to the at least one spoon blade; and/or
    the operating device comprises a ratchet mechanism arranged to maintain a position of the operating device after operation by a user and a decoupling device that can be operated by the user for decoupling the ratchet mechanism allowing the ratchet mechanism to reset.

14. The assembly according to claim 12, wherein, in use, the operating device is moved toward the distal end of the vaginal speculum, thereby moving the reusable electric device toward the distal end of the vaginal speculum.

15. The assembly according to claim 12, wherein the operating device has near a proximal end thereof an operating device notch arranged to be engaged by an operator to operate the operating device and wherein the connection system is arranged to position a proximal end of the reusable electric device near the operating device notch.

16. The assembly according to claim 12, wherein the reusable electric device has interface means near a proximal end of the reusable electric device positioned close to an operating device notch.

17. The assembly according to claim 1, wherein the connection system comprises a guiding rail.

* * * * *